| United States Patent [19] | [11] Patent Number: 4,857,466 |
|---|---|
| Saunders et al. | [45] Date of Patent: Aug. 15, 1989 |

[54] PROBE FOR DETECTION OF SPECIFIC HUMAN LEUKEMIAS

[75] Inventors: Grady F. Saunders; Wendy M. Mars, both of Houston, Tex.

[73] Assignee: The Board of Regents of the University of Texas System, Austin, Tex.

[21] Appl. No.: 94,099

[22] Filed: Sep. 4, 1987

Related U.S. Application Data

[63] Continuation of Ser. No. 655,942, Sep. 28, 1984, abandoned.

[51] Int. Cl.$^4$ .......................... C12N 1/20; C12N 1/00
[52] U.S. Cl. ............................... 435/252.33; 435/320; 436/813; 935/73
[58] Field of Search .................. 435/6, 91, 172.3, 253, 435/320, 849; 436/63, 64, 94, 501, 813; 935/2, 11, 29, 56, 73, 78, 80; 536/27

[56] References Cited

U.S. PATENT DOCUMENTS

| | | | |
|---|---|---|---|
| 4,167,556 | 9/1979 | Selhub et al. | 424/1 |
| 4,192,917 | 3/1980 | Zurawski, Jr. | 435/236 |
| 4,273,757 | 6/1981 | Selhub et al. | 424/1 |
| 4,358,535 | 11/1982 | Falkow et al. | |
| 4,424,201 | 1/1984 | Valinsky et al. | 424/3 |
| 4,542,096 | 9/1985 | Leder | 935/78 X |
| 4,562,159 | 12/1985 | Shafritz | 436/811 X |
| 4,599,305 | 7/1985 | Witte et al. | |

OTHER PUBLICATIONS

Shtivelman, E. et al. Nature 315 13 Jun. 1985, pp. 550–554.
Lewin, B. (editor) In: Genes, John Wiley & Sons, NY, 1983, pp. 297–298.
Srinivasan, A. et al., Proc. Natl. Acad. Sci USA, 78, 1981, pp. 2077–2081.
Srinivasan, A. et al. Proc. Natl. Acad. Sci USA, 79, 1982, pp. 5508–5512.
Selden, J. R. et al. Proc. Natl. Acad. Sci USA 80, 1983, pp. 7289–7292.
Collins, S. J. et al., Science 225, 1984, pp. 72–74.
Birnie, G. D., et al., "A New Approach to the Classification of Human Leukaemias: Measurement of the Relative Abundance of A Specific RNA Sequence by Means of Molecular Hybridisation", The Lancet, 1983, pp. 197–200.
Wiedemann, L. M., "Differences Among the Polyadenylated RNA Sequences of Human Leucocyte Populations: An Approach to the Objective Classification of Human Leukaemias", The EMBO Journal, vol. 2, No. 1, pp. 9–13, 1983.
Abstract of "Identification of Sequences Preferentially Transcribed in Chronic Myelonenous Leukemia", Mars., W. M., et al, Cellular and Molecular Biology of Neoplasia, Oct. 2–6, 1983.
Mars, W. M., et al., Abstract of "A Preferentially Transcribed Sequence in Chronic Myelogenous Leukemia and Ph$^1$+Acute Leukemia", Penn St., Aug. 1–3, 1984.
Mars, W. M., et al. Abstract of "A Preferentially Transcribed in Chronic Myelongenous Leukemia and Ph$^1$+Acute Leukemia", Grad. School, 9/84.
Saunders, G., et al., Abstract of "Use of Gene Probes in the Diagnosis and Classification of Myeloid Leukemias", Prevention and Detection of Cancer, 6th International Symposium Vienna, Austria, Nov. 26–29, 1984.
Mars., W. M., et al., Paper by "Preferentially Expressed Genes In Chronic Myelogenous Leukemia", preprint *Blood*, May, 1985.

*Primary Examiner*—Johnnie R. Brown
*Assistant Examiner*—Jeremy M. Jay
*Attorney, Agent, or Firm*—Arnold, White & Durkee

[57] ABSTRACT

Gene probes containing genetic sequences that code for proteins which are phenotypically characteristic of certain leukemias, such as chronic myelogenous leukemia, can be prepared from RNA of a person having that disease. The gene probes can be used in diagnostic hybridization tests with RNA of a patient to be diagnosed.

1 Claim, No Drawings

PROBE FOR DETECTION OF SPECIFIC HUMAN LEUKEMIAS

This is a continuation of application Ser. No. 655,942, filed Feb. 26, 1986, now abandoned.

BACKGROUND OF THE INVENTION

The present invention relates to a method of diagnosing certain leukemias. More specifically, it concerns a method of detecting an RNA sequence which represents a protein or proteins which are phenotypically characteristic of certain leukemias.

Approximately 88% of the patients with clinically typical chronic myelogenous leukemia (CML) have a cytogenetic abnormality known as the Philadelphia chromosome (Ph[1]). This aberration has also been reported at a much lower frequency in both acute lymphocytic leukemia (ALL) and acute myelogenous leukemia (AML). Chromosome banding techniques have shown the Ph[1] chromosome to be a shortened chromosome 22 with a break occurring in bands q11. In 92% of the patients with Ph[1]-positive CML, the missing piece of chromosome 22 attaches distally to the long arms of chromosome 9, band q34, in what has been shown to be a reciprocal translocation. Of the Ph[1]-positive variants with a different type of alteration, 4% are known to have complex translocations which again involve chromosome 9.

Specific karyotype abnormalities are also associated with other kinds of malignancies. For example, other types of human and murine leukemias and lymphomas have been correlated with particular cytogenetic changes. Additionally, it is known that certain leukemias with distinct cytogenetic changes display constitutive expression of proteins which are normally regulated during myeloid differentiation. Thus, phenotypic subcategories of leukemia, as defined by karyotype abnormalities, can additionally be defined by protein alterations which in turn may reflect the cellular populations of RNA.

Since preferred treatments differ for different malignancies, there is always a need for methods of diagnosis which are improvements in terms of speed, reliability, and/or cost. The present invention provides an improved diagnostic method by using genetic engineering techniques to detect genetic sequences coding for phenotypically characteristic proteins.

The genetic engineering techniques used relate to the recent advances in recombinant DNA technology which have facilitated the isolation of specific genes or parts thereof and their transfer to bacteria, yeast, plant, or animal cells and to the viruses that infect these organisms. The transferred gene material (or modified gene) is replicated and propagated as the transformed cell or viruses replicate.

The transfer and expression of genes or portions thereof between viruses, eukaryotes, and prokaryotes is possible because the DNA of all living organisms is composed of the same four nucleotides. The basic differences reside in the sequences in which the nucleotides appear in the genome of the organism. Specific nucleotide sequences, arranged in codons (nucleotide triplets), code for specific amino acid sequences. However, the coding relationship between an amino acid sequence and a DNA nucleotide sequence is essentially the same for all organisms.

Many recombinant DNS techniques employ transfer vectors. A transfer vector is a DNA molecular which contains genetic information which insures its own replication when transferred to a host microorganism strain. Plasmids are an example. "Plasmid" is the term applied to any autonomously replicating DNA unit which might be found in a microbial cell, other than the genome of the host cell itself. A plasmid is not genetically linked to the chromosome of the host cell. Plasmid DNA's exist as double stranded ring structures. A plasmid DNA ring may be opened and a fragment of heterologous DNA inserted and the ring reclosed. Thus, transfer vectors serve as a carrier or vector for an inserted fragment of heterologous DNA.

Transfer is accomplished by a process known as transformation. During transformation, host cells mixed with plasmid DNA incorporate into themselves entire plasmid molecules. Once a cell has incorporated a plasmid, the latter is replicated within the cell and the plasmid replicas are distributed to the daughter cells when the cell divides. Any genetic information contained in the nucleotide sequence of the plasmid DNA can be expressed in the host cell. Typically, a transformed host cell is recognized by its acquisition of traits carried on the plasmid, such as resistance to certain antibiotics. Any given plasmid may be made in quantity by growing a pure culture of cells containing the plasmid and isolating the plasmid DNA therefrom.

Restriction enzymes are also frequently used in these techniques. They are hydrolytic enzymes capable of catalyzing site-specific cleavage of DNA molecules. The locus of restriction enzyme action is determined by the existence of a specific nucleotide sequence. Such a sequence is termed the recognition site for the restriction enzyme. Since any DNA susceptible of cleavage by such an enzyme must contain the same recognition site, the same cohesive ends will be produced by the cleavage. Therefore, it is possible to join heterologous sequences of DNA which have been treated with a restriction endonuclease to other sequences similarly treated. Restriction sites are relatively rare, but the general utility of restriction endonucleases has been greatly amplified by the chemical synthesis of double stranded oligonucleotides bearing the restriction site sequence. Therefore, virtually any segment of DNA can be coupled to any other segments simply by attaching the appropriate restriction oligonucleotide to the ends of the molecule, and subjecting the product to the hydrolytic action of the appropriate restriction endonuclease, thereby producing the requisite cohesive ends.

Other methods for DNA cleavage or for end sequence modification are also available. A variety of nonspecific endonucleases may be used to cleave DNA randomly. End sequences may be modified by creation of oligonucleotide tails of dA on one end and dT at the other, or a dG and dC, to create sites for joining without the need for specific linker sequences.

The term "expression" is used in recognition of the fact that an organism ordinarily does not make use of all of its genetically endowed capabilities at any given time. Even in relatively simple organisms such as bacteria, many proteins which the cell is capable of synthesizing are not synthesized, although they may be synthesized under appropriate environmental conditions. When the RNA that codes for a given protein is being synthesized by the organism, that RNA is said to be expressed. The RNA synthesis will eventually lead to the synthesis of the corresponding protein.

The use of these techniques in the present invention is described below.

SUMMARY OF THE INVENTION

A diagnostic method in accordance with the present invention includes the steps of preparing a gene probe which includes genetic sequences that code for proteins which are phenotypically characteristic of myelogenous leukemia; annealing denatured DNA from the gene probe to RNA of a patient to be diagnosed; and determining whether hybridization occurs. "Gene probe" is used in this patent to mean a vector, either by itself or within a host, which includes the genetic sequences described above. DNA can be isolated from the gene probe and tested for hydridization with RNA of a patient. Hybridization between the two indicates that the same genetic sequences appear in the sample from the patient as in the probe. Since those genetic sequences code for proteins that have been found to be phenotypically characteristic of certain leukemias, a positive result from the hybridization tests indicates that the patient may be suffering from one of those particular diseases.

In one embodiment of the present invention, the gene probe includes genetic sequences that code for proteins which are phenotypically characteristic of chronic myelogenous leukemia.

One clone prepared using the methods of the present invention, designated C-A3 (ATCC No. 39868), has been studied with 63 different RNA samples. A genetic sequence contained in this clone has been found to code for a protein or proteins which are highly expressed in the chronic phase of both Ph[1]-positive and Ph[1]-negative CML, as well as in a Ph[1]- positive AML. Expression is reduced in lymphoblastic crisis of CML (L BC-CML) and is essentially absnt in myeloblastic crisis of CML (M BC-CML). These results suggest that this probe may be useful in diagnosing Ph[1]-negative CML and in distinguishing M BC-CML from L BC-CML and Ph[1]-positive AML.

The present invention should complement conventional laboratory techniques for diagnosing certain leukemias. It is possible that results of diagnostic tests in accordance with the present invention could be determined in as little as one day.

DETAILED DESCRIPTION OF SPECIFIC EMBODIMENTS

The following is an example of how to prepare and use gene probes in accordance with the present invention. Those skilled in the art will recognize that modifications could be made that would achieve the same result.

I. Construction of a cDNA Library

A. RNA Extraction and Purification

Total RNA was isolated from a patient suffering from chronic phase, Ph[1]-positive CML, using the procedure described in Frazier, et al., "Efficient Extraction of RNA from Mammalian Tissue", Molecular and Cellular Biochemistry, 56:113-122 (1983). (This and the other publications cited in this patient are incorporated herein by reference.) The patient was male and had blood type Opositive. He exhibited the common 9:22 translocation in 100% of the metaphases recovered from his bone marrow. All stages of myeloid differentiation were represented in the sample utilized for library construction, with a preponderance of the leukocytes in the myelocyte or more mature categories.

A 195 ml sample with a cell count of $4.06 \times 10^8$/ml was collected by leukapheresis. The red blood cells were lysed with a solution containing 144 mM NH$_4$Cl, 17mM TrisHCl pH 7.2, and the leukocytes were isolated by centrifuging. The pellets were extracted with 112 ml of a buffer solution consisting of 75 mM NaCl, 25 mM Na$_2$EDTA, 0.1% Sarkosyl NL-97 (INC Pharmaceuticals, Inc., Plainview, New York), and 10 mM Tris (pH 8.0), combined with 88 ml of phenol saturated with buffer. This mixture was then centrifuged for 20 minutes at 5000 rpm and 4° C. using a Sorvall GSA rotor.

The aqueous phase was removed and incubated with 100 μg/ml proteinase K (catalog no. 24568-10, E.M. Biochemicals, Cincinnati, Ohio) for one hour at 37° C. The digests were then extracted with 50 ml of phenol saturated with the buffer solution described above and 50 ml of sevag solution (chloroform/isoamyl alcohol; 48:2, v/v). This mixture was centrifuged for 20 minutes at 5000 rpm and 4° C. in a GSA rotor. The aqueous phase was removed from the sample and the nucleic acid was precipitated with 2 volumes of 95% ethanol and 1/25 volume of 5 M NaCl.

The precipitates were collected by centrifugation, and then were resuspended in 45 ml of sterilized water and 90 ml of 4.5 M sodium acetate and placed overnight at −20° C. The centrifugation and resuspension steps were repeated until the sample was DNA free. After the final precipitation, the sample was resuspended in sterile H$_2$O.

Poly (A+) RNA was selected by oligo (dT) chromatography using essentially the procedures described in Munjaal, et al., "Isolation and Characterization of Pre-proinsulin mRNA from Fetal Bovine Pancreatic Islets," Molecular and Cellular Endocrinology, 15:51-60 (1979). Two columns were set up with oligo (dT) cellulose Type III (Collaborative Research Corp., San Diego, Calif.). Both were washed with water and 0.1 N sodium hydroxide and equilibrated with a binding buffer solution which contained 10 mM Tris, 0.5 M sodium chloride, 1 mM EDTA, and 0.5% Sarkosyl, pH 7.5.

After the sample was heated to 68° C., the RNA was mixed with an equal volume of 2X binding buffer and passed through the columns. The mixture that passed through the columns was collected and run through again. The columns were then washed with binding buffer to remove unbound RNA. Elution of the bound RNA was performed with an elution buffer which contained 10 mM Tris, 1 mM EDTA, and 0.5% Sarkosyl pH 7.5. The columns were then washed extensively with elution buffer and equilibrated with binding buffer.

Poly (A+) RNA which was passed over a column once was heated to 68° C. for 5 minutes, added to an equal volume of 2X binding buffer, and repassed through the oligo dT column. Elution was done as before. Precipitation was caused by adding 2 volumes of 100% ethanol and 1/25 volume of 5 M sodium chloride, and holding this mixture at −80° C. for 1 hour. After thawing, the samples were centrifuged at 17,500 rpm for 30 minutes at 4° C. to separate supernatant from the pellets, using an HB-4 rotor.

B. Synthesis of Single Strand cDNA

Single strand cDNA with a $^3$H-dCTP (deoxycytidine triphosphate) tracer was prepared from 10 μg of the poly (A+) RNA in a 400 μl reaction containing 50 mM Tris-HCl, pH 8.3; 9 mM magnesium acetate; 50 mM potassium chloride; 20 mM dithiothreitol (DTT); 50 μCi $^3$H-dCTP (24.8 Ci/mmol); 750 μM each of dATP (deoxyadenosine triphosphate), dCTP, dGTP (deoxyguanosine triphosphate), and dTTP (deoxythymidine triphosphate); 400 μM sodium pyrophosphate; 11.4 μg actinomycin D; 10 μg oligo (dT)$_{12-18}$ primer; and 180 units of reverse transcriptase (Life Sciences, St. Petersburg, Fla.). This mixture was incubated at 46° C. for 20 minutes, and was then adjusted to 0.3 N sodium hydroxide in a 30 μl volume, incubated at room temperature overnight to permit RNA hydrolysis, and then adjusted to pH 7.

C. Second Strand Synthesis

This synthesis generally followed the procedure described by Efstratiadis, et al., "Enzymatic In Vitro Synthesis of Globin Genes," Cell 7:279 (1976). The 40 μl reaction contained the single stranded cDNA; 50 μCi $^{32}$PdCTP as a tracer; 120 mM potassium phosphate buffer, pH 6.9; 10 mM magnesium chloride; 10 mM DTT, and 500 μM each of dATP, dTTP, dCTP, and dGTP; along with 22.5 units of E. Coli DNA polymerase I holoenzyme. The reaction mixture was incubated at 15° C. for 6 hours and 15 minutes.

Single strand regions were removed by treatment with 50 units S1 nuclease (Miles Laboratories, Napersville, Ill.), in a buffer containing 300 mM NaCl; 50 mM NaOAc, pH 4.5; and 1 mM ZnCl$_2$ at 37° C. for 30 minutes.

D. Recombination and Transformation pBR322 plasmid was used, which has the characteristics of resistance to tetracycline and ampicillin. The restriction enzyme Pst I was used to cut the circular plasmid DNA inside the ampicillin resistant gene.

The plasmid DNA was then dG tailed. RNAse A which had been heat treated to kill any DNAse present was added. Forty μl (3.36 μg) of the pBR, 20 μl of 1M potassium cacodylate, 1 μl of bovine serum albumin (BSA) (50 μg/μl); 8 μl of 100 mM magnesium chloride; 1 μl of 100 mM BME (β-mercaptoethanol); 1 μl of 10 mM dGTP; 0.8 μl (20 units) of terminal deoxynucleotidyl transferase; and 28.2 μl of distilled water were mixed to give a total reaction volume of 100 μl. The mixture was incubated at 37° C. for 1.5 hours. Tail length was calculated by including a $^3$H-dGTP tracer.

The double stranded cDNA from the previous steps was dC tailed by mixing 10 μl of 1M potassium cacodylate; 5 μl of 10 mM cobalt chloride; 1 μl of 5 mM dCTP; 1 μl of 50 mM BME; 25 ng of BSA; 14.75 μl of water; 14.75 μl of the DNA; and 1 μl (approximately 12 units) of terminal deoxynucleotidyl transferase, and incubating the mixture at 37° C. for 3.5 minutes. Tail length was estimated by including a $^3$H-dCTP tracer.

The dC tailed double stranded cDNA was annealed to the dG tailed pBR322, which had already been linearized at the Pst I restriction site as described above. Equimolar amounts of the two (approximately 0.028 μg of the former and 0.47 μg of the latter; $1.67 \times 10^{-7}$ moles of each) were diluted to 125 μl in annealing buffer (300 mM NaCl; 1 mM EDTA; 10 mM Tris-HCl, pH 7.5). The mixture was incubated at 66° C. for 5 and ¾ hours, then allowed to cool to room temperature slowly overnight in a water bath.

E. coli strain RRI cells were transformed by mixing the chimeric plasmid produced above with calcium treated cells, followed by 1.5 minute heat shock treatment at 42° C. This was followed by a five fold dilution with L-broth and incubation for 1 hour at 37° C. The solution was plated onto L-agar plates and transformed colonies were allowed to grow up overnight at 37° C. Supplementing the L-agar with 12.5 μg/ml tetracycline permitted selection of the colonies which had been transformed. After the initial transformation, supplementation with 50 μg/ml of ampicillin permitted detection of the ones which were ampicillin sensitive, and therefore had the cDNA insert. The colonies so selected were used as a "library" for screening.

II. Screening the cDNA Library

The colonies were grown for 8 to 12 hours at 37° C. on nitrocellulose filters placed on tetracycline-supplemented L-Agar plates. The filters were then transferred to similar plates containing 200 μg/ml of chloramphenicol for an additional 12–16 hour incubation period. The filters were then denatured and fixed using the procedure described in Grunstein, et al., "Colony Hybridization: A Method for the Isolation of Cloned DNA's that Contain a Specific Gene," Proc. Natl. Acad. of Sci. U.S.A., 72:3961 (1975), omitting the fixation steps described in that article from proteinase K treatment onward. A piece of Whatman's 3 MM paper was soaked with solutions of 0.5M sodium hydroxide and 1.5M sodium chloride, and then the filters were placed on top of the paper to soak. The filters were dried, soaked once again, dried again, and then soaked with paper that had been soaked in a 1.0 M Tris solution, pH 7.4. Finally, the filters were soaked on paper containing 1.0 M Tris, pH 7.4; 0.5 M NaCl. After further drying, the filters were baked for 3 to 6 hours at 68° C.

The filters were prehybridized in 400 ml of solution containing 120 ml of 20X SSC (1X SSC=0.15 M NaCl, 0.015 M Na$_3$ citrate), pH 7.0; 16 ml of 50X Denhardt's solution; and the balance distilled water.

Hybridization occurred in a solution containing 9 ml of 20X SSC, pH 7.0; 1.2 ml of 50X Denhardt's; 150 μl of 200 mM EDTA; 1.5 ml of 10% Sarkosyl; and distilled water to make a total volume of 30 ml. The filters were placed in bags, 4 filters per bag, with 10 ml of the hybridization solution and 50 μl of radiolabelled single strand cDNA.

The radiolabelled cDNA had been prepared by mixing 10 μl of homologous RNA (2.5 ug) with 2.5 μl of 1 M TrisHCl, pH 8.3; 3.0 μl of oligo dT$_{12-18}$ primer (500 μg/ml); 4.0 μl of 100 mM magnesium acetate; 2.5 μl of 1 M potassium chloride; 5.0 μl of 0.1 M DTT; 0.5 μl each of 50 mM dGTP, 50 mM dTTP, 50 mM dATP, and 5 mM dCTP; and 6.25 μl of actinomycin D (400 μg/ml). The reaction also contained 300 μCi of $^{32}$P-dCTP (S.A. 3000 Ci/mmole) which had been dried down and 2.5 μl of reverse transcriptase (22.5 units). Incubation was for 25 minutes at 46° C.

Approximately $1.0 \times 10^6$ radioactive counts were added per ml of hybridization solution. The mix was incubated at 68° C. overnight. After washing for 6 hours at 68° C. with 1X SSC; 0.5% Sarkosyl, the filters were rinsed with 1X SSC. The filters were then exposed to x-ray films for 1 to 3 days at −70° C. in the presence of intensifying screens.

417 colonies out of a total of 729 (57.2%) displayed a hybridization signal more intense than control colonies containing plasmid pBR322 without a cDNA insert, indicating that the recombinant plasmids which transformed the parent cells of those 417 colonies contained middle or highly repetitive RNAs from the CML patient. These 417 colonies were used for further screening.

This subset library was then screened against $^{32}$P cDNA's transcribed from leukocyte poly (A+) RNAs of patients with chronic phase, Ph$^1$-positive CML, mixed blastic crisis CML (M BC-CML and L BC-CML), acute myelomonocytic leukemia (AMML), and human placenta. The screening procedure was largely as described above. Sixteen colonies of the 417 in the subset library showed little or no hybridization with the placenta and AMML-derived probes. The results for those 16 are shown in Table 1.

TABLE 1

HYBRIDIZATION INTENSITY OF SELECTED CML cDNA CLONES WITH $^{32}$P-cDNA FROM DIFFERENT TISSUES

| Clone | Homologous CML | Chronic Phase CML | Mixed M/L BC-CML | AMML | Human Placenta |
|---|---|---|---|---|---|
| C-A3 | ++ | ++ | − | +/− | − |
| C-A4 | ++ | ++ | − | − | − |
| C-B1 | ++ | + | + | − | +/− |
| D-D1 | ++ | ++ | − | +/− | − |
| E-B4 | ++ | ++ | − | +/− | +/− |
| E-D4 | ++ | − | − | − | +/− |
| E-E3 | ++ | − | + | +/− | +/− |
| E-F5 | + | − | + | − | +/− |
| E-H5 | ++ | + | − | − | − |
| F-F1 | + | ++ | ++ | − | − |
| G-H2 | + | + | + | − | +/− |
| G-H3 | + | + | − | − | − |
| H-E2 | ++ | + | − | − | +/− |
| H-G1 | + | − | − | +/− | − |
| J-E5 | + | + | − | +/− | − |
| J-F1 | ++ | + | − | +/− | − |

Plasmids isolated from 8 of the colonies listed in Table 1 were radiolabelled with $^{32}$P and hybridized to nitrocellulose filters (Northern Blots) containing total RNA extracted from normal and leukemic leukocytes. Filters containing immobilized RNA were prepared by size fractionating the RNA through agarose denaturing gels and transferring it to nitrocellulose paper. By utilizing a constant amount of RNA in the denaturing gels, it was possible to compare the relative message abundance of samples on the filters as well as to estimate the size of the RNA molecules with homology to the recombinant plasmid. Reutilization of the filters helped determine whether recombinants contained cDNA inserts transcribed from the same RNA molecules and provided evidence that lack of detectable signal was not due to degradation or incomplete transfer of the RNA. Plasmids containing homologous cDNAs would be expected to hybridize with RNAs of the same size and relative abundance on a given filter.

In the Northern Blot analysis, total RNA was isolated from peripheral blood leukocytes obtained by venapuncture of leukapheresis as described in Frazier, et al., supra, or by utilizing a minor modification where DNA was removed by DNAse (Worthington) treatment. Plasmid was isolated from individual colonies and separated from cleared lysate by cesium chloride-ethidium bromide density ultracentrifugation. nitrocellulose filters were prepared, prehybridized, hybridized, and washed as described in Thomas, "Hybridization of Denatured RNA and Small DNA Fragments Transferred to Nitrocellulose," Proc. Natl. Acad. Sci. U.S.A., 77:5201 (1980), using 2–10 μg of glyoxylated total RNA from each sample.

The RNA samples were applied to vertical 1.2% or 1.5% agarose gels, electrophoresed for 8 hours at 50 volts, and transferred to nitrocellulose paper overnight. The filters were baked for 2 hours in a vacuum oven at 80° C., then prehybridized nd hybridized with sheared calf thymus DNA. The plasmid was nick translated to high specific activity (0.5–2.0×10$^8$ cpm/μg.) with [$^{32}$P]-dCTP and added to the hybridization solution at 2.0×10$^6$ cmp/ml. Initial filter washes were performed at room temperature with 2 final washes for 15 minutes each at 42° C. The filters were air dried, then exposed to X-ray film for 1 to 7 days at room temperature, −20° C., or −70° C. in the presence of intensifying screens.

The results indicated that 6 of the 8 plasmids tested in this manner represent RNA sequences preferentially expressed in the Ph$^1$-positive leukemias. Sequence G-H3 (approx. 1000 NT; "NT" is the number of nucleotide residues) was highly expressed in the M BC-CML and moderately expressed in one chronic phase CML. F-F1 (approx. 750 NT) was moderately expressed in L BC-CML and highly expressed in the chronic phase CMLs. E-B4 RNA (approx. 700 NT) was moderately represented in all chronic phse CMLs and the L BC-CML. Although E-B4 and F-F1 hybridized to the same samples, these recombinant clones could be distinguished reproducibly since the RNAs were present at substantially different concentrations. D-D1 (approx. 1500 NT) was moderately expressed in all the Ph$^1$-positive samples tested including both the samples in blastic crises. Clone C-A4 (approx. 720 NT) displayed low to moderate hybridization with the chronic phase CMLs. C-B1 failed to hybridize with any of the RNAs whereas H-G1 hybridized at low levels with all of them.

Because of the initial observation that the recombinant clone C-A3 represented sequences moderately transcribed in L BC-CML and highly expressed in all chronic phase CMLs, it was tested further. Total RNA was prepared from the peripheral blood leukocytes of a larger sampling of patients with various types of leukemias and used in additional hybridization experiments. The samples tested with C-A3 included four AMMLs, one AML, three ALLs, three CLLs, a Ph$^1$-negative CML, a Ph$^1$-positive AML, a myeloproliferative disorder (MPD) (Table 2, sample 40a), eight Ph$^1$-positive CMLs in chronic phase, one M BC-CML, one L BC-CML, and two different pools of normal peripheral blood leukocytes from a total of 24 donors. The MPD patient was considered distinguishable from Ph$^1$-negative CML because the laboratory assay for leukocyte alkaline phosphatase (LAP) was normal or elevated rather than decreased.

No hybridization of C-A3 was detectable with filters containing 5-10 μg of total RNA from the normal RNAs, one AMML, the ALLs and one CLL after a 3 day exposure. A very faint signal could be seen with the M BC-CML, two CLLs, three AMMLs, and the AML (Table 2, Samples 19, 23, 24, 32, 33, 34, and 37). Intense hybridization was evident after a 1 day exposure of the filters with only 2 ug of total RNA from the eight $Ph^1$-positive CML patients in chronic phase, the $Ph^1$-negative CML, and the $Ph^1$-positive AML. A moderate signal was detectable in the patient with L BCCML where a white cell differential disclosed that 31% of the cells were blasts. There was no detectable hybridization with the All, the MPD patient, the myeloblastic crisis (76% blasts) and the normal RNAs. Multiple transcript sizes were present in some of the samples. Expression did not appear to correlate with clinical or laboratory data or the therapy status.

Since total RNA extraction requires numerous cells and does not specifically select for cytoplasmic RNA, on 11 of the samples utilized for total RNA extraction as well as on several additional ones, a modification of the procedure for preparation of cytoplasmic RNA from small numbers of leukocytes described in White, et al., "Simple Analysis of Relative mRNA levels in Multiple Small Cell or Tissue Samples," J. Biol. Chem. 257:8569 (1982), was used. RNA was directly blotted onto nitrocellulose paper, bound and then hybridized with radiolabelled probe C-A3.

In this procedure, leukocytes were isolated from whole peripheral blood or leukapheresis specimens by pelleting the cells and lysing the erythroid elements. Cytoplasmic RNA was then prepared using a modification of the procedure described in White, supra. $5 \times 10^6$ cells were resuspended in 43 μl of a cold buffer consisting of 10 mM Tris-HCl and 1 mM EDTA, pH 8.0. One μl each of 100 mM DTT and RNAsin (25 units/ul, Biotec) were added to inhibit RNAse activity. Cells were enucleated by adjusting to 0.5% with 5.0% NP-40 (Shell Corp.), incubating 5 minutes at 0° C., and pelleting the nuclei. The cytoplasma supernatant was mixed with an equal volume of $12 \times SSC/14.8\%$ formaldehyde incubated at 65° C. for 30 minutes and then stored at −70° C. Filters were prepared by diluting 5 μl of the sample to 150 μl with $15 \times SSC$, applying the RNA by vacuum filtration to nitrocellulose soaked in $15 \times SSC$ using a Minifold II slot blotter system (Schleicher and Schuell) and baking under a vacuum for 2 hours at 80° C. Prehybridization, hybridization, and washes were performed as described for Northern Blots.

Consistent with the results obtained from the glyoxal gel experiments, the peripheral blood samples from the $Ph^1$-positive AML, the L BC-CML and 11 of 12 chronic phase CMLs were positive after a brief exposure of the filter for autoradiography. The negative CML sample (Table 2, Sample 17) was obtained from a treated patient who had a blood differential and white count resembling that of a normal individual, although the LAP value was still decreased and $Ph^1$-positive metaphases were were present in the bone marrow. Two other samples of myeloid origin were also posible. One was a diploid AML (Table 2, Sample 38) with 94% blast cells in the differential and a normal LAP value. The other was the later of 2 samples obtained from the MPD patient (Table 2, Sample 40b). A longer exposure of the filter failed to reveal a signal with the other samples tested with the exception of two CLLs and one ALL (Table 2, Samples 25, 26 and 28). This ALL patient presented with 10% $Ph^1$-positive hyperdiploid cells in the marrow prior to therapy.

The results of the testing with peripheral blood samples is sumarized in Table 2. In addition to the abbreviations already defined, AMoL' (acute monocytic leukemia) is used in the table.

TABLE 2

| Sample No. | PERIPHERAL BLOOD SAMPLES Diagnosis | Result with C-A3 |
|---|---|---|
| 1 | CML | POS |
| 2 | CML | POS |
| 3 | CML | POS |
| 4 | CML | POS |
| 5 | CML | POS |
| 6 | CML | POS |
| 7 | CML | POS |
| 8 | CML | POS |
| 9 | CML | POS |
| 10 | CML | POS |
| 11 | CML | POS |
| 12 | CML | POS |
| 13 | CML | POS |
| 14 | CML | POS |
| 15 | CML | POS |
| 16 | CML | POS |
| 17 | CML | NEG |
| 18 | CML | POS |
| 19 | M BC-CML | +/− |
| 20 | M/L BC-CML | NEG |
| 21 | L BC-CML | POS |
| 22 | L BC-CML | POS |
| 23 | CLL | +/− |
| 24 | CLL | +/− |
| 25 | CLL | +/− |
| 26 | CLL | +/− |
| 27 | CLL | NEG |
| 28 | ALL | +/− |
| 29 | ALL | NEG |
| 30 | ALL | NEG |
| 31 | ALL | NEG |
| 32 | AMML | +/− |
| 33 | AMML | +/− |
| 34 | AMML | +/− |
| 35 | AMML | NEG |
| 36 | AML | POS |
| 37 | AML | +/− |
| 38 | AML | POS |
| 39 | AMoL | NEG |
| 40a | MPD | NEG |
| 40b | MPD | POS |
| 41 | normal | NEG |
| 42 | normal | NEG |
| 43 | normal | NEG |
| 44 | normal | NEG |
| 45 | normal | NEG |

Results obtained with the bone marrow samples were less dramatic, as can be seen from Table 3.

TABLE 3

| No. | BONE MARROW SAMPLES Diagnosis | C-A3 |
|---|---|---|
| 1 | CML | POS |
| 2 | CML | POS |
| 3 | CML | POS |
| 4 | CML | POS |
| 5 | CML | POS |
| 6 | CML | POS |
| 7 | CML | POS |
| 8 | CML | POS |
| 9 | CML | NEG |
| 10 | M BC-CML | NEG |
| 11 | CLL | POS |
| 12 | CLL | +/− |
| 13 | MPD | POS |
| 14 | MPD | +/− |
| 15 | normal | POS |
| 16 | normal | POS |

TABLE 3-continued

BONE MARROW SAMPLES

| No. | Diagnosis | C-A3 |
|---|---|---|
| 17 | normal | POS |
| 18 | normal | +/− |

None of the negative results were due to degradation since all samples showed positive hybridization with different RNA probes.

Certain points are significant about the results of the tests with the C-A3 probe. First, more than one transcript size was detected in some of the samples. While the implications of this are presently unclear, it may simply reflect the fact that total cellular RNA was utilized for these studies and the larger band is a nuclear RNA precursor of the processed mRNA. Second, while it was derived from a cDNA library made from a Ph$^1$-positive CML patient, the hybridization profile of a Ph$^1$-negative CML patient (Table 2, Sample 18) is similar to that found with the Ph$^1$-positive CMLs. This provides molecular evidence for the phenotypic similarity of different CML populations. One of the C-A3 positive CML specimens utilized in the studies (Table 2, Sample 3) contained a complex translocation involving chromosomes 9, 11, and 22, and two of the samples which were either C-A3 negative or only faintly positive (Table 2, Samples 30 and 32) had cytogenetic abnormalities involving the long arms of chromosome 9. These combined data imply that the problem of C-A3 expression could be more complex than a simple correlation with gross chromosal changes. The possibility remains, however, that similar changes have occurred in the DNA of C-A3 positive patients which are only detectable at the molecular level.

An examination of the differentials and white blood cell counts of the samples shows that C-A3 expression is unlikely to be solely related to the presence of immature myeloid elements although these cells are likely to be capable of producing the C-A3 message. Two specimens which contained immature myeloid cells (other than blasts) failed to produce a detectable signal on autoradiograms (Table 2, Sample 40a; Table 3, Sample 9). Additionally, some of the samples which produced faint positives with clone C-A3 did not contain immature myeloid cells (Table 2, Samples 24-26) which suggests that cells other than those from the myeloid lineage can produce this mRNA. Since the genetic defect in CML is thought to occur in a multipotent stem cell, it is not surprising that low level transcription of C-A3 sequences can occur in multiple cell types. However, it appears that the highest transcription levels occur in CML, specifically in the chronic phase.

The clinical data on patient from which Samples 40a and 40b in Table 2 were taken is notable since the second sample (40b) was positive. When the patient was first examined, the cytogenetic data indicated a dividing diploid population, the LAP was elevated (265) and although the marrow was suggestive of CML, the diagnosis was not definite. On a follow-up visit 12 months later, the dividing cell population was still diploid, the LAP was normal, and mild splenomegaly was noted. At this time, sample 40a was obtained from a therapeutic white cell depletion. This sample was negative for expression of CA3. Five months later the patient returned with symptoms of gross splenomegaly and newly developed hepatomegaly. ALthough the LAP was still normal (177), standard therapy for CML was begun since the disease was becoming more aggressive. A sample obtained prior to initiation of therapy was found to be positive for C-A3 message. Two weeks later, the LAP value had dropped significantly (to 97) although it was still within our normal laboratory values. The data suggests that the patient had a developing Ph$^1$-negative CML. It appears to be highly significant that the expression of clone C-A3 could be correlated with the course of this disease.

A detectable difference was found in the C-A3 levels of blst crisis CML patients. Five patients were studied after entering blast crisis: two with L BC-CML, two with M BC-CML and one mixed crisis patient with both lymphoblasts and myeloblasts. Surprisingly, the patients with M BC-CML and the mixed crisis patient had significantly lower levels of C-A3 than the patients with L BC-CML. While additional blast crisis samples need to be studied, these results indicate that C-A3 represents an additional means of testing for differences between two seemingly similar populations of cells. This is important since the prognosis and therapy for M BC-CML and L LB-CML patients differ.

Additionally, it was found that a patient with Ph$^1$-positive AML hd high levels of C-A3, whereas the marrow of a "poor prognosis" CML patient (Table 3, Sample 9) was negative. It is possible that C-A3 expression reflects an inherent state of the myeloid leukemia cells which is predictive for patient response to common therapy regimens.

The preceeding description is intended to illustrate the present invention. It is not intended to describe all possible embodiments of the invention.

We claim:

1. *E. coli* (ATCC no. 39868) which has been transformed by a recombinant plasmid that includes genetic sequences that code for proteins for which the corresponding mRNA is moderately or highly abundant in chronic myelogenous leukemia.

* * * * *

UNITED STATES PATENT AND TRADEMARK OFFICE
CERTIFICATE OF CORRECTION

PATENT NO. : 4,857,466
DATED : August 15, 1989
INVENTOR(S) : Grady F. Saunders and Wendy M. Mars It is certified that error appears in the above-identified patent and that said Letters Patent is hereby corrected as shown below:

In column 2, line 1, "DNS" should be --DNA--.

In column 2, line 2, "molecular" should be --molecule--.

In column 3, line 36, "absnt" should be --absent--.

In column 3, line 63, "patient" should be --patent--.

In column 4, line 9, "INC" should be --ICN--.

In column 4, line 22, "sample" should be --samples--.

In column 5, line 23, "E. Coli" should be --E. Coli--.

In column 8, line 1, "nd" should be --and--.

In column 8, line 5, "cmp" should by --cpm--.

In column 8, line 40, "phse" should be --phase--.

UNITED STATES PATENT AND TRADEMARK OFFICE
CERTIFICATE OF CORRECTION

PATENT NO. : 4,857,466
DATED : August 15, 1989
INVENTOR(S) : Grady F. Saunders and Wendy M. Mars It is certified that error appears in the above-identified patent and that said Letters Patent is hereby corrected as shown below:

In column 9, line 14, "All" should be --ALL--.

In column 11, line 33, "chromosal" should be

--chromosomal--.

In column 12, line 26, "blst" should be --blast--.

In column 12, line 39, "hd" should be --had--.

Signed and Sealed this

Twenty-seventh Day of April, 1993

*Attest:*

MICHAEL K. KIRK

*Attesting Officer*  Acting Commissioner of Patents and Trademarks